(12) United States Patent
Butz et al.

(10) Patent No.: US 8,827,925 B2
(45) Date of Patent: Sep. 9, 2014

(54) PRICKING DEVICE AND METHOD FOR TAKING A BLOOD SAMPLE

(75) Inventors: Marion Butz, Regensburg (DE); Andreas Knie, Regensburg (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 181 days.

(21) Appl. No.: 12/996,205

(22) PCT Filed: May 29, 2009

(86) PCT No.: PCT/EP2009/056594
§ 371 (c)(1), (2), (4) Date: Mar. 18, 2011

(87) PCT Pub. No.: WO2009/147080
PCT Pub. Date: Dec. 10, 2009

(65) Prior Publication Data
US 2011/0208091 A1   Aug. 25, 2011

(30) Foreign Application Priority Data

Jun. 6, 2008   (DE) .......................... 10 2008 027 267
Aug. 21, 2008  (DE) .......................... 10 2008 039 111

(51) Int. Cl.
A61B 5/00   (2006.01)
A61B 5/15   (2006.01)

(52) U.S. Cl.
CPC ............. *A61B 5/1433* (2013.01); *A61B 5/1411* (2013.01)
USPC ............ 600/583; 600/573; 606/181; 606/182

(58) Field of Classification Search
USPC ............................ 600/572–584; 606/181–182
See application file for complete search history.

(56) References Cited

U.S. PATENT DOCUMENTS

| 4,643,189 | A | | 2/1987 | Mintz |
| 4,924,879 | A | * | 5/1990 | O'Brien ........................ 600/583 |
| 5,527,334 | A | | 6/1996 | Kanner et al. |
| 5,938,679 | A | * | 8/1999 | Freeman et al. .............. 606/181 |
| 5,951,582 | A | | 9/1999 | Thorne et al. |

(Continued)

FOREIGN PATENT DOCUMENTS

| DE | 19909602 A1 | 9/2000 |
| DE | 19948759 A1 | 4/2001 |

(Continued)

OTHER PUBLICATIONS

English Translation of JP 64-042010, Toji Mukai et al., Mar. 14, 1989.*

(Continued)

*Primary Examiner* — Rene Towa
(74) *Attorney, Agent, or Firm* — Lathrop & Gage LLP

(57) ABSTRACT

The invention relates to a pricking device (1) for taking a blood sample, comprising a movable holding device (10) for pricking means (5), a linear guide element (11) for guiding the movable holding device, means (12) for driving the movable holding device and a release device (31) for releasing the pricking movement (6) of the pricking means. When the release device has been manually actuated, the movable holding device can be moved in a translatory manner by the drive means. Said drive means comprise a curved path (20) in which the movable holding means is directly engaged, enabling the pricking device to have a particularly simple structure.

17 Claims, 4 Drawing Sheets

(56) References Cited

U.S. PATENT DOCUMENTS

Figure 8:
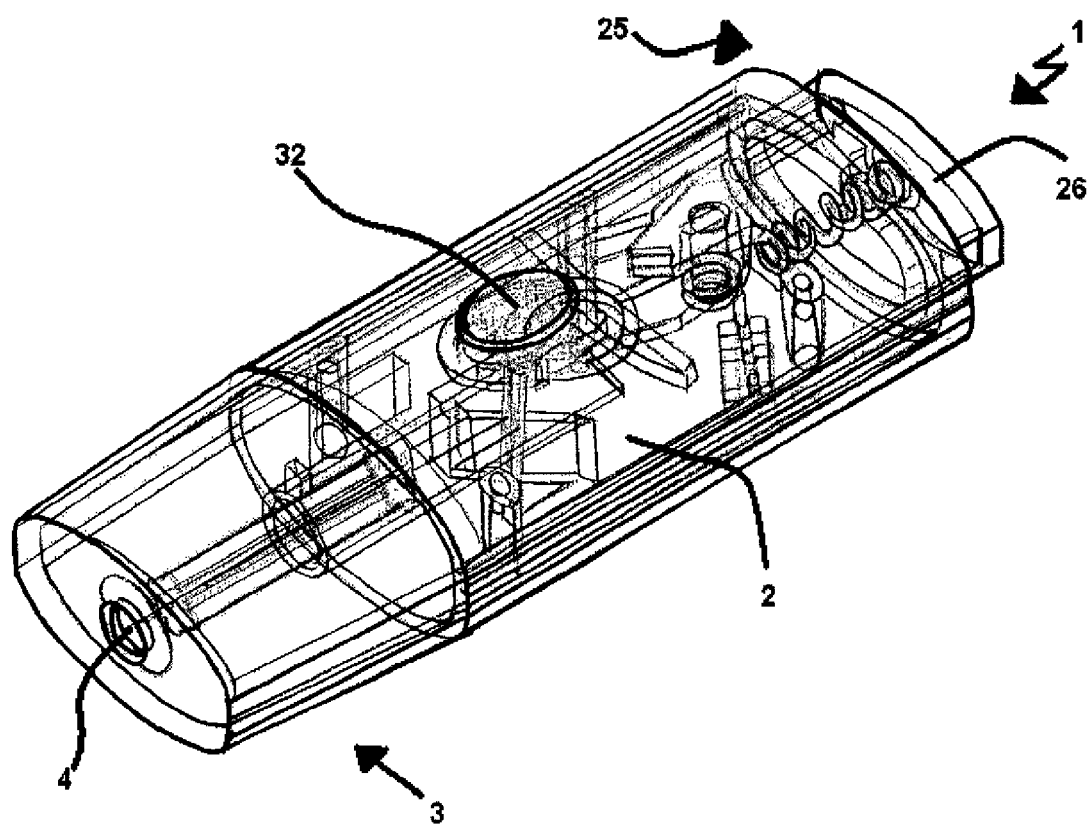

| | | | |
|---|---|---|---|
| 5,954,738 | A | 9/1999 | LeVaughn et al. |
| 5,997,561 | A * | 12/1999 | Bocker et al. ............ 606/182 |
| 6,221,089 | B1 | 4/2001 | Mawhirt |
| 6,409,740 | B1 | 6/2002 | Kuhr et al. |
| 6,419,661 | B1 | 7/2002 | Kuhr et al. |
| 7,842,060 | B2 | 11/2010 | List |
| 2005/0131441 | A1 | 6/2005 | Iio et al. |
| 2005/0145520 | A1 | 7/2005 | Ilo et al. |
| 2006/0155317 | A1 | 7/2006 | List |
| 2006/0200181 | A1 * | 9/2006 | Fukuzawa et al. ........ 606/181 |
| 2010/0168618 | A1 | 7/2010 | List |

FOREIGN PATENT DOCUMENTS

| | | | |
|---|---|---|---|
| EP | 0898936 | A2 | 3/1999 |
| EP | 1090584 | A2 | 4/2001 |
| EP | 1669028 | A | 6/2006 |
| JP | 64-42010 | * | 3/1989 |
| WO | 2005/077275 | A1 | 8/2005 |

OTHER PUBLICATIONS

International Search Report for PCT/EP2009/056594, mailed Sep. 7, 2009.
International Search Report for PCT/EP2009/056597, mailed Sep. 7, 2009.
Examination Report for European Patent Application No. 09 757 462.8, mailed Mar. 8, 2012.
International Search Report for International Application No. PCT/EP2009/056594, dated Sep. 7, 2009.
English translation of the Written Opinion of the International Searching Authority, mailed Dec. 16, 2010, for International Application No. PCT/EP2009/056594.
First Page of Examination Report corresponding to Chinese Patent Application No. 200980120168.3, mailed Oct. 8, 2012—includes English translation.
Russian Examination Report, Russian Application No. 2010153803/14(077801), Mar. 28, 2013, 5 pages, in Russian.
Russian Examination Report, Russian Application No. 2010153803/14(077801), Mar. 28, 2013, 4 pages, English translation.

\* cited by examiner

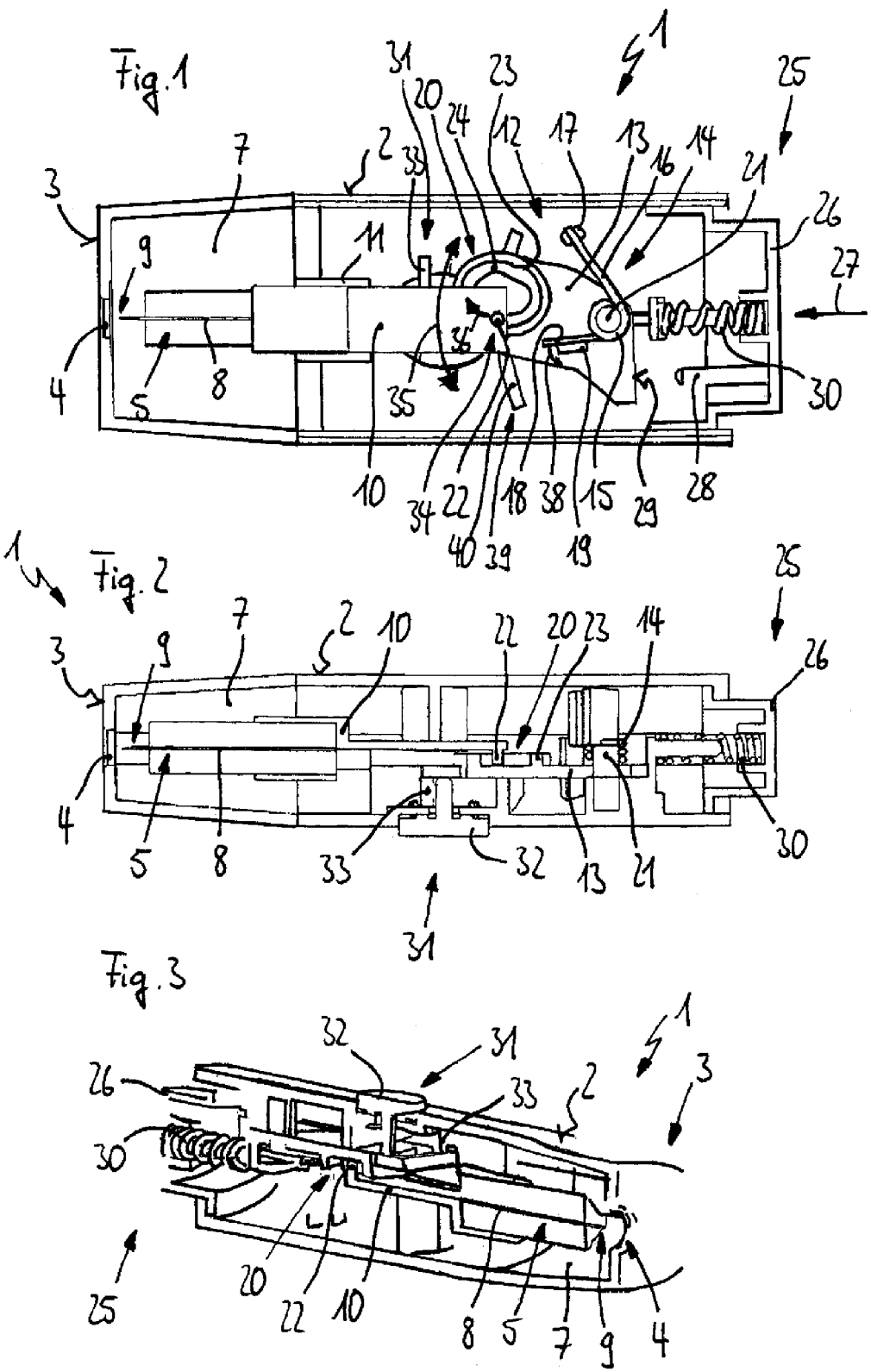

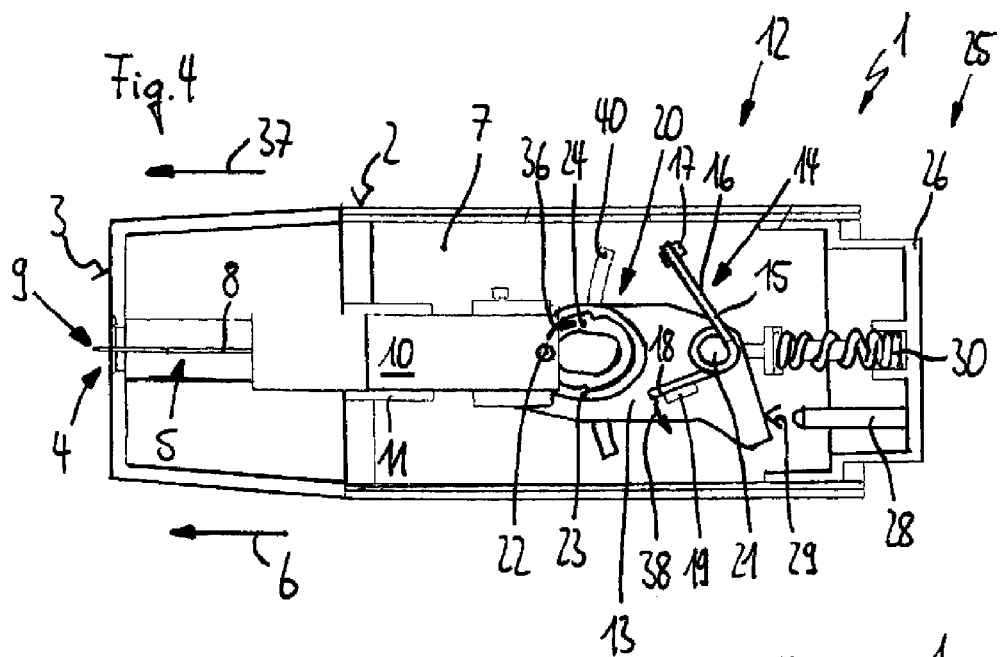
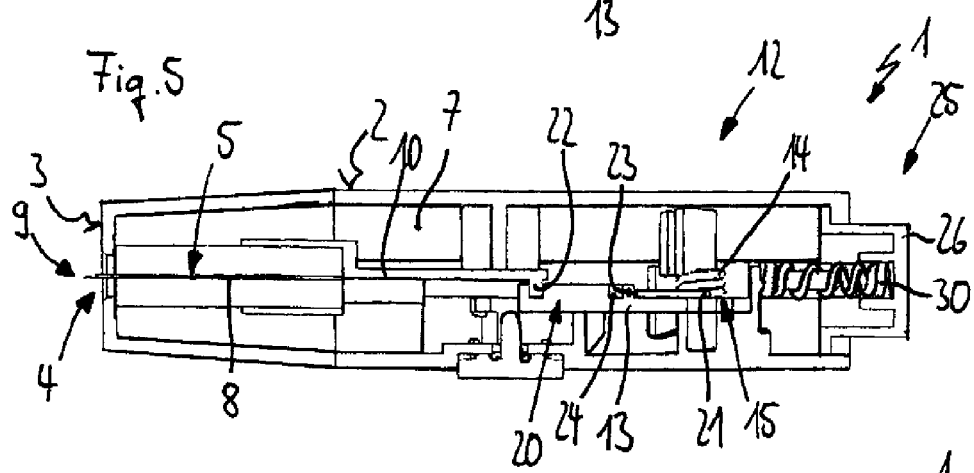
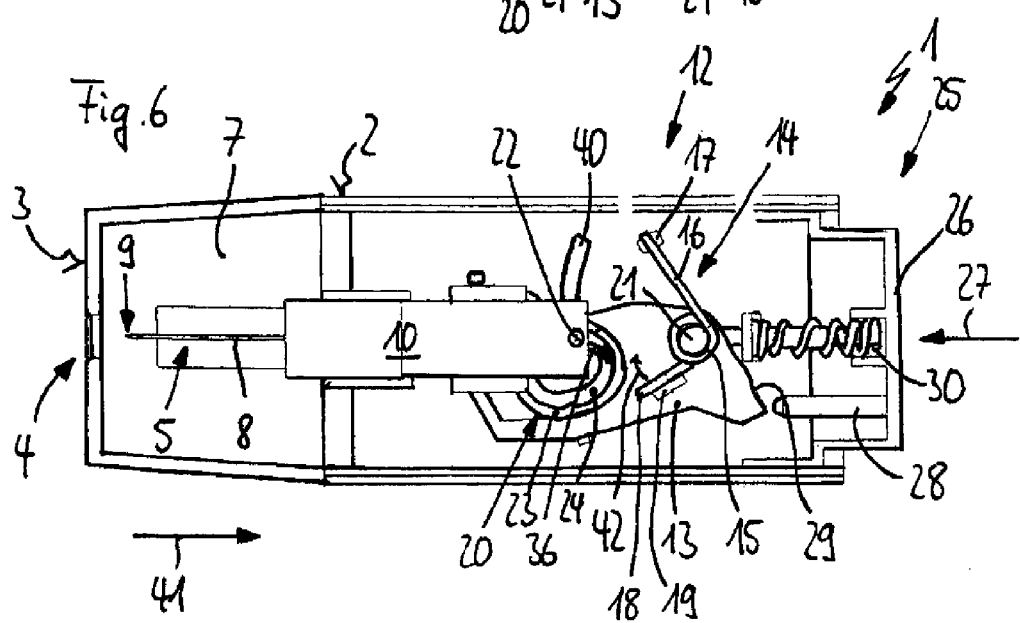

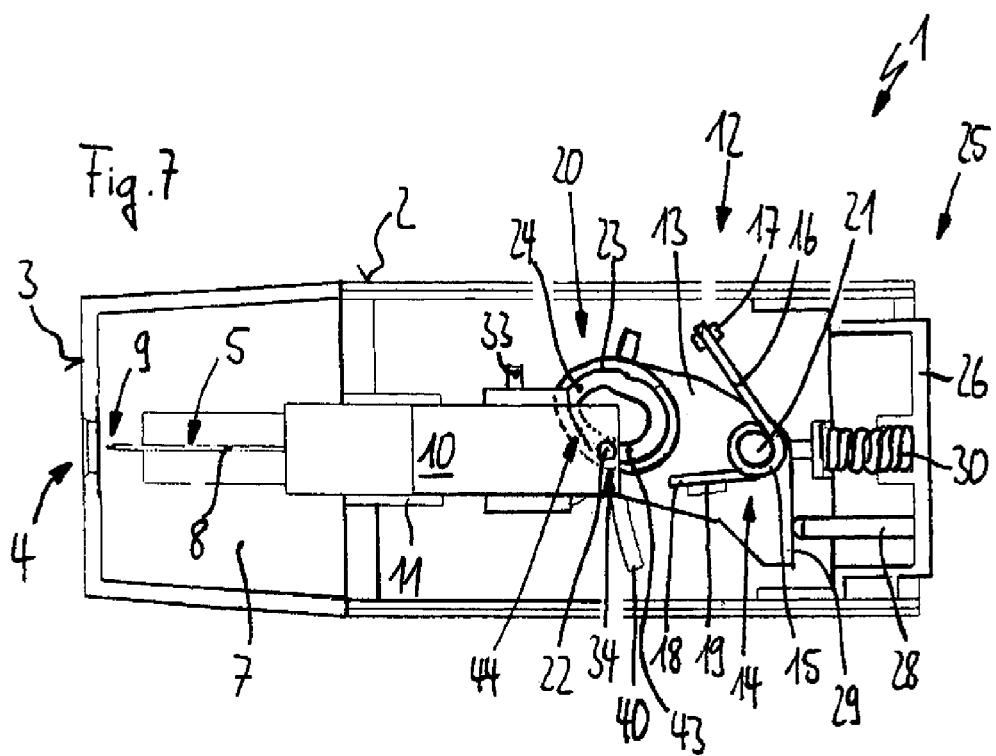

PRICKING DEVICE AND METHOD FOR TAKING A BLOOD SAMPLE

CROSS-REFERENCE TO RELATED APPLICATIONS

This application is a U.S. National Stage Application under 35 U.S.C. §371 of International Application No. PCT/EP2009/056594, filed May 29, 2009, which claims the benefit of German Application No. 102008027267.1, filed Jun. 6, 2008 and German Application No. 102008039111.5, filed Aug. 21, 2008. All three of these applications are hereby incorporated by reference in their entireties.

DESCRIPTION

The invention concerns firstly a pricking device for taking a blood sample with a moveable holder device for a pricking means, with a linear guide to guide the moveable holder device, with means for driving the moveable holder device and with a trigger device to trigger the pricking movement of the pricking means, wherein after manual activation of the trigger device the moveable holder device can be moved translationally by means of the drive means. Secondly the invention concerns a method for taking a blood sample in which a pricking means is moved forward and then immediately backward, whereby the pricking means can briefly penetrate a body at least with its tip, wherein the pricking aid is guided translationally in a moveable holder device and wherein the moveable holder device is driven by a spring drive.

Generic devices are well known from the prior art. They are used preferably for taking blood samples in order to be able to perform medical tests on the blood drop, for example measuring the blood sugar. For this such a device can be placed on a patient's skin area in order to allow insertion in the skin of a suitable pricking means, such as an interchangeable lancet of the device, whereby after pricking by the pricking means one or more drops of blood can be taken from the damaged capillary vessels in the upper skin layers. In order to reduce the damage to the skin layers as far as possible, such pricking means are often moved forward and back translationally along a pricking axis. For example patent specification U.S. Pat. No. 5,527,334 describes a generic pricking aid in which a needle or lancet is held by a needle holder, wherein the needle holder is mounted mobile linearly between two guide ribs inside the pricking aid. The needle is driven by a tensionable torsion spring which is attached firstly with a first leg end in the housing of the pricking aid and secondly with a second leg end in a moving coupling part of the pricking aid. The coupling part is connected by a first end area by form fit but resiliently with the needle holder and mounted by a second end area in a guide slot. When the torsion spring is released by manual activation of a corresponding trigger device, the second end area of the coupling part can be moved along the guide slot, whereby the coupling part can move the needle holder linearly forward and back. As a result the needle can in turn execute a pricking movement in which the needle tip can briefly accelerate out of the housing of the pricking aid.

The object of the invention is to refine such generic pricking devices, frequently also called pricking aids, for taking blood samples.

The object of the invention is achieved by a pricking device for taking a blood sample with a moveable holder device for a pricking aid, with a linear guide for guiding the moveable holder device, with means for driving the movable holder device and with a trigger device for triggering a pricking movement of the pricking aid, in which after manual operation of the trigger device the moveable holder device can be moved translationally by means of the drive means, whereby the pricking device is characterised in that the drive means have a curved track in which the moveable holder device engages directly.

If the holder device engages directly in a curved track of the drive means, the construction of the pricking device can be kept very simple. Thus the pricking device can be constructed particularly flat. In particular no additional coupling devices are required between the holder device and the drive means, so that smaller masses must be accelerated and/or decelerated during the pricking movement of the pricking aid or holder device. As a result a pricking movement can be performed substantially faster, whereby the puncture pain can be reduced. Advantageously the holder device is driven translationally by means of the curved track so that a translational pricking movement, such as of a lancet, can be achieved by means of the curved track. The curved track serves here as a guide curve for the holder device concerned.

Suitable pricking means can be any structure such as lancets or needles which can penetrate suitably easily into the upper skin layers. A pricking means can for example be moved forward and back only along a straight track and/or along a curved track.

Evidently the course of the curved track here can be selected and designed in many ways in order to move the holder device advantageously. A movement course along the curved track is particularly simple if the curved track is formed in a closed loop. Consequently an excellent embodiment also provides that the curved track is an endless curved track. In particular the benefits explained in connection with the curved track can also be transferred to the endless curved track. In particular with an endless curved track, the drive means can perform a particularly even drive movement, whereby the pricking result of the pricking means in relation to the body, such as on the upper skin layers, can be substantially improved.

In this connection the object of the invention is also achieved by a method for taking a blood sample in which a pricking means is moved forwards and then directly back, whereby the pricking means can penetrate briefly into a body at least with its tip, wherein which the pricking means is guided translationally in a moveable holder device, and wherein the moveable holder device is driven by a spring drive, wherein the moveable holder device is guided directly inside and along an endless curved track of a control curved track element.

Advantageously in such a closed endless curved track the holder device moves only in a single peripheral direction, whereby the entire movement kinematics of the mobile components within the pricking device can be simplified. In particular because of such movement kinematics, the reverberation of the pricking means on the pricking movement can be reduced or ideally even fully excluded, whereby the risk of secondary pricking by the pricking means can be further reduced. As a result the pricking process can take place substantially less painfully. To this extent the taking of a blood sample can be made substantially more comfortable for the patient.

The spring drive can be provided easily and very compactly if the drive means comprise a spring element for storage of energy.

Preferably the spring element can be constructed relatively flat as a leg spring.

Furthermore an advantageous method variant provides that the holder device is moved only in a single peripheral direction along the curved track both on the forward movement of the pricking means and on the return movement of the pricking means. In particular this extremely effectively reduces the risk of reverberation of the moveable holding device.

A preferred embodiment variant in this respect thus provides that the drive means comprise a curved track element which comprises the endless curved track. This allows particularly good guidance of the endless curved track.

If the control curved track element of the drive means is mounted swivelably about a swivel axis, the holder device can be mounted so that it is easily moveable translationally on the linear guide.

Therefore with regard to a further advantageous method variant, it is provided that the curved track is swivelled along an arc section about a swivel axis, whereby the moveable holder device is moved translationally. A swivel movement in this respect can be initiated advantageously by means of a leg spring.

If also the spring element is mounted on a swivel axis of a control curved track element, the construction of the present pricking device can be further simplified.

Preferably the curved track is formed oval, whereby an acceleration and speed profile with regard to the holder device of the pricking means can be further influenced. In particular the holder device can be accelerated substantially better in straighter sections of an oval curved track, so that as a result in particular a faster forward movement of the pricking aid or holder device can be achieved. This is presumably because in the straighter areas of the oval curved track, there is less friction between the holder device and the guide areas of the curved track.

A further advantageous embodiment provides that the curved track has a side guiding element within which the holder device is at least partly arranged and guided. If the curved track has a side guiding element, for example in the form of a groove, the holder device can be guided particularly reliably along the curved track.

The holder device can engage particularly simply in the curved track, in particular in the guiding element, if the holder device has a curve follower. Such a curve follower can very easily be produced by means of a guide peg which engages in the guiding element. Preferably the guide peg is formed by the holder device itself. For example a curve follower is moulded on the holder device in an injection moulding method. Evidently the curve follower can also be connected with the holder device in another way.

If the curve follower of the holder device can always only move in one peripheral direction along the curved track both on the translational forward movement of the holder device and on the translational return movement of the holder device, only by means of the present holder device can an essentially circular drive motion be transferred directly into a linear output movement.

Such a transfer of movement can be achieved very well if a curve follower of the holder device is arranged inside a profile of a curved track such that the curve follower is mounted mobile inside the profile only in a single peripheral direction along the curved track. Also the movement kinematics of the pricking means on a pricking device can be executed advantageously.

In particular a good trigger safety of the present pricking device can be guaranteed if the curve follower of the holder device is arranged in a starting position inside the curved track, and the curved track with regard to the starting position has a inlet area for the curve follower and an outlet area for the curve follower, wherein the inlet area and outlet area are different. The operating reliability of the pricking device can be further improved if the curve follower is in a starting position such that when the pricking device is in a state ready for operation, on triggering of the pricking device the curve follower can move out of the start position over the outlet area, and after the pricking means has performed a pricking movement, it can return via the inlet area to the starting position.

Further advantages, objectives and properties of the present invention are explained in the description below with reference to the enclosed drawing which shows as an example a pricking device for taking a blood sample with a pricking means which can be operated repeatedly.

The drawing shows:

FIG. 1 diagrammatically a first cross-section view of a pricking device for taking a blood sample in a state ready for operation in which a curve follower of a holder device is arranged in a starting position inside a curved track of a control curved track element;

FIG. 2 diagrammatically a further cross-section view of the pricking device in the state ready for operation of FIG. 1;

FIG. 3 diagrammatically a perspective cross-section view of the pricking device in the state ready for operation of FIGS. 1 and 2;

FIG. 4 diagrammatically a cross-section view of the pricking device in a pricking position of a pricking means of the pricking device;

FIG. 5 diagrammatically a further cross-section view of the pricking device in the pricking position in FIG. 4;

FIG. 6 diagrammatically a cross-section view of the pricking device in a rest position after performing a pricking movement and in an untensioned state;

FIG. 7 diagrammatically a cross-section view of a pricking device during a pricking process with spring drive again tensioned, and FIG. 8 diagrammatically a perspective view of the housing of the pricking device from FIGS. 1 to 7.

The pricking device 1 shown in FIGS. 1 to 8 for taking blood samples has a flat housing 2 (see in particular FIG. 8) on the underside 3 of which a treatment opening 4 is provided through which for treatment a pricking means 5 can be accelerated briefly out of a housing interior 7 of the pricking device 1 in a pricking movement 6 (see FIGS. 4 and 5). The pricking device 1 is a pricking device 1 which can be operated repeatedly, which after successful pricking, allows the pricking means 5 to be retracted again into the housing 2 immediately and then the pricking device 1 can be pre-tensioned again in order to be operated a second time.

The pricking means 5 in the form of a pricking needle 8, after successfully piercing the upper skin layer of a patient, is retracted again immediately into the flat housing 2 so there is no further risk of injury from the tip 9 of the pricking needle 8.

The pricking means 5 is held by a suitable moveable holder device 10, often called a lancet holder, wherein the moveable holder device 10 can be moved forward and back translationally by means of a linear guide 11 along a fictitious pricking axis which is embodied by the pricking needle 8.

So that the pricking means 5 can ideally always perform an almost identical pricking movement 6, the pricking device 1 has further means 12 for driving the moveable holder device 10.

These drive means 12 in this embodiment example comprise in particular a control curved track element 13 and a spring element 14 in the form of a leg spring 15. The spring element 14 is here clamped with a first leg 16 in a housing holder 17 and with a second leg 18 in a holder 19 of the control curved track element 13 so that it can be tensioned.

The drive means 12 furthermore have a curved track 20 in which the moveable holder device 10 engages directly. The curved track 20 is here allocated to the control curved track element 13. So that the holder device 10 can follow the curved track 20 reliably when the control curved track element 13 is swivelled about a swivel axis 21, the holder device 10 forms a curve follower 22 which is arranged in a guiding element 23 of the curved track 20. The curved track 20 in itself is formed as an oval endless curved track 24 on the control curved track element 13 so that the curve follower 22 can also follow the curved track 20 endlessly in just one direction.

In order to be able to move the control curved track element 13 manually such that the spring element 14 can be pre-tensioned with a sufficiently great spring force, on the top 25 of the flat housing 2 is provided a manually activatable button 26 which can be pressed into the flat housing 2 along arrow direction 27. During such activation the curved track element 13 can be moved, the spring element 14 pre-tensioned and the entire pricking device 1 transferred to a tensioned state ready for operation as shown in FIG. 1. During the tensioning process a button element bar 28 of the manually activatable button element 26 can press against a projection 29 of the control curved track element 13, whereby the control curved track element 13 is swivelled about the swivel axis 21. As a result the spring element 14 is tensioned. The button element 26 can then be moved back to its starting position (see FIG. 1) by means of a coil spring 30.

In order to be able to trigger the pricking device 1, the pricking device 1 has a suitable trigger device 31 which comprises a pusher 32 (see for examples FIGS. 2 and 3) with a locking arm 33. The locking arm 33 can suitably correspond with the moveable holder device 10 so that the moveable holder device 10 is locked with the locking arm 33, in particular when the spring element 14 is pre-tensioned. As a result a pricking movement 6 can be prevented as long as the pusher 32 of the trigger device 31 is not activated and the trigger device 31 is not triggered.

According to the depictions in FIGS. 1 to 3, the pricking device 1 is in a tensioned state ready for operation in which the curve follower 22 inside the guiding element 23 is in a starting position 34 on the curved track 20. The geometries and interplay of the control curved track element 13, curved track 20, the swivel ability 35 of the control curved track element 13 and hence the curved track 20, the holder device 10 and the curve follower 22 are selected such that the curve follower 22 can move only in one peripheral direction 36 along the curved track 20. In particular as a result it can be guaranteed that the holding device 10 with the pricking means 5 cannot reverberate after the actual pricking movement 6, so it is ensured that per activation of the pricking device 1, the pricking means 5 can only reach through the treatment opening 4 a single time.

To trigger the pricking device 1 ready for operation, the pusher 32 is activated manually whereby the locking arm 33 releases the control curved track element 13. The holder device 10 can then perform a translational forward movement 37 (see FIG. 4) in the sense of the pricking movement 6, initiating the translational forward movement 37 and associated possible pressurisation of the pricking means 5 by the spring force or a spring movement 38 of the expanding leg spring 15 or the spring movement 38 of the second leg 18 of the spring leg 15. The spring movement 38 swivels the control curved track element 13 about the swivel axis 21. The control curved track element 13 is thus guided additionally in a guide 39 along an arc section 40.

Due to the swivel movement of the control track element 13, the curve follower 22 follows the curved track 20 along peripheral direction 36 and the holding device 10 with pricking means 5 can perform the pricking movement 6. According to the depictions in FIGS. 4 and 5, the pricking device 1 is shown in a pricking state in which the holder device 10 is deflected to a maximum in its translation forward movement 37. The curve follower 22 is here in a position closest to the treatment opening 4.

Advantageously on a translational return movement 41 of the holder device 10, at the same time the curve follower 22 is guided in the continued forward peripheral direction 36, as shown in particular in the view in FIG. 4. This immediate translational return movement 41 is also made possible by the still expanding leg spring 15. Consequently there is never an essentially reversed movement of the curve follower 22 within the curved track 20 of the control curved track element 13. Rather the curve follower 22 always moves further in the clockwise direction along the curved track 20 until the pricking device 1 reaches a rest state in an untensioned state, as shown in the view in FIG. 6.

Now the pricking device 1 can be re-tensioned for a further pricking movement 6 in that the manually activatable button element 26 is pushed in direction of arrow 27, whereby the spring element 14 can be re-tensioned i.e. compressed with a tension movement 42. In this tensioning process the curve follower 22 moves further along the curved track 20 in the peripheral direction 36 until the curve follower 22 has moved back to its starting position 34, the spring element 14 is pre-tensioned and the pricking device 1 is again ready for use as shown in the view in FIG. 7. Here too an inlet area 43 for the curve follower 22 on the curved track 20 and an outlet area 44 for the curve follower 22 on the curved track 22 are marked. The curve follower 22 runs through the outlet area 44 only when the pricking device 1 is triggered, when the curve follower 22 leaves its starting position. Curve follower 22 only runs through the inlet area 43 when the pricking device 1 or spring element 14 is tensioned and the curve follower 22 is moved into the starting position 34. To this extent the inlet area 43 and outlet area 44 are different areas of the curved track 20.

Advantageously the holder device 10 with the present pricking device 1 engages directly in the curved track 20 so that a rotational movement of swivel movement of the control curved track element 13 can be converted directly with very little loss into a translational pricking movement 6 of the holding device 10.

Advantageously a substantially oval curved track is used here with regard to the control curved track element 13 in order to allow maximum acceleration of the curve follower 22 and hence the pricking means 5 in the forward and subsequently in the reverse direction in the straighter sections of the substantially oval curved track 20. This ideally allows a further reduction of the puncture pain.

The curved track 20 essentially serves as a guide curve for the holding device 10 and its triggering. Thus the pricking means 5 can only pierce the skin once and not—as in previous spring-guided systems—lead to reverberation and thus secondary pricking or repeated piercing of the skin. Also the entire structure of the present pricking device 1 advantageously has a particularly flat design as all essentially moveable components can be formed flat and are low in number. In particular only one curve follower 22 is required, which is also arranged in a guiding element 23 and thus requires no additional construction height inside the pricking device 1.

All features disclosed in the application documents are claimed as essential to the invention as they where novel individually or in combination in relation to the prior art.

List of References

1. Pricking device
2. Housing
3. Underside
4. Treatment opening
5. Pricking means
6. Pricking movement
7. Housing interior
8. Pricking needle
9. Pricking needle tip
10. Moveable holder device
11. Linear guide
12. Drive means
13. Control curved track element
14. Spring element
15. Leg spring
16. First leg
17. Housing holder
18. Second leg
19. Holder of control curved track element
20. Curved track
21. Swivel axis
22. Curve follower
23. Guiding element
24. Endless curved track
25. Top side
26. Manually activatable button element
27. Arrow direction
28. Button element bar
29. Projection
30. Coil spring
31. Trigger device
32. Trigger
33. Locking arm
34. Starting position
35. Swivel capacity
36. Peripheral direction
37. Translational forward movement
38. Spring movement
39. Guide
40. Arc section
41. Translational return movement
42. Tension movement
43. Inlet area
44. Outlet area

The invention claimed is:

1. Pricking device for taking a blood sample comprising a moveable holder device attached to a pricking means, a linear guide for guiding the moveable holder device, drive means for driving the moveable holder device and a trigger device for triggering a pricking movement of the pricking means, wherein after manual activation of the trigger device the moveable holder device is configured to be moved translationally by means of the drive means, wherein the drive means have a curved track that the moveable holder device engages directly, wherein the drive means further comprise a control curved track element mounted swivelable about a swivel device that is exterior to the curved track, and wherein the control curved track element is moveable along an arced guide that is mounted exterior to the curved track, wherein the curved track is swivelable about the swivel device and the moveable holder device is moveable translationally.

2. Pricking device according to claim 1, characterized in that the curved track is an endless curved track.

3. Pricking device according to claim 1, characterized in that the curved track is formed oval.

4. Pricking device according to claim 1, characterized in that the curved track has a guiding element inside which the moveable holder device is at least partly arranged and guided.

5. Pricking device according to claim 1, characterized in that the moveable holder device has a curve follower.

6. Pricking device according to claim 1, characterized in that a curve follower of the moveable holder device is moveable only in a peripheral direction along the curved track both on a translational forward movement of the moveable holder device and on a translational return movement of the moveable holder device.

7. Pricking device according to claim 1, characterized in that a curve follower of the moveable holder device is arranged inside a guiding element of a curved track such that the curve follower inside the guiding element is mounted moveable only in a single peripheral direction along the curved track.

8. Pricking device according to claim 1, characterized in that a curve follower of the moveable holder device is arranged inside the curved track in a starting position, and the curved track with regard to the starting position has an inlet area for the curve follower and an outlet area for the curve follower, wherein the inlet area and the outlet area are different from each other.

9. Pricking device according to claim 1, characterized in that the drive means comprises a spring element for storage of energy.

10. Pricking device according to claim 9, characterized in that the spring element comprises a leg spring.

11. Pricking device according to claim 9, characterized in that the spring element is mounted on the swivel device.

12. Pricking device according to claim 1, further comprising a tensioning mechanism including a coil spring.

13. Pricking device according to claim 1, characterized in that the curved track is a substantially planar endless curved track configured to provide a continuous rate of movement for the moveable holder device.

14. A method for taking a blood sample comprising a step of drawing blood from a subject using the pricking device of claim 1.

15. Method for taking a blood sample, comprising a step of drawing blood from a body in which a pricking means moves forward and then directly backward, whereby the pricking means at least with a tip thereof briefly penetrates the body, the pricking means being guided translationally in a moveable holder device and the moveable holder device being driven by a spring drive, wherein the moveable holder device is guided directly inside and along a curved track of a control curved track element mounted swivelable about a swivel device that is exterior to the curved track and wherein the control curved track element moves along an arced guide that is mounted exterior to the curved track, whereby the curve track swivels about the swivel device and the moveable holder device is moves translationally so that the pricking means at least with a tip thereof briefly penetrates the body.

16. Method according to claim 15, characterized in that the moveable holder device always moves only in a single peripheral direction along an endless curved track both on a translational forward movement of the pricking means and on a translational reverse movement of the pricking means.

17. Method according to claim 15, characterized in that the curved track is an endless curved track swiveled along an arc section about the swivel device, whereby the moveable holder device moves translationally.

* * * * *